United States Patent [19]

Greenwald et al.

[11] Patent Number: 5,547,981
[45] Date of Patent: Aug. 20, 1996

[54] TAXOL-7-CARBAZATES

[75] Inventors: Richard B. Greenwald, Somerset; Annapurna Pendri, Matawan, both of N.J.

[73] Assignee: Enzon, Inc., Piscataway, N.J.

[21] Appl. No.: 198,194

[22] Filed: Feb. 17, 1994

Related U.S. Application Data

[63] Continuation-in-part of Ser. No. 140,346, Oct. 20, 1993, abandoned, and Ser. No. 28,743, Mar. 9, 1993, abandoned.

[51] Int. Cl.$^6$ .................. A61K 31/335; C07D 305/14
[52] U.S. Cl. .................. 514/449; 549/510; 549/511; 528/421
[58] Field of Search .................. 549/510, 511; 514/449; 528/421

[56] References Cited

U.S. PATENT DOCUMENTS

| | | | |
|---|---|---|---|
| 4,101,380 | 7/1978 | Rubinstein et al. | 195/63 |
| 4,680,338 | 7/1987 | Sundoro | 525/54.1 |
| 4,814,470 | 3/1989 | Colin et al. | 514/449 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,019,504 | 5/1991 | Christen et al. | 435/123 |
| 5,157,049 | 10/1992 | Haugwitz | 514/449 |
| 5,227,400 | 7/1993 | Holton | 514/444 |
| 5,229,526 | 7/1993 | Holton | 549/213 |

FOREIGN PATENT DOCUMENTS

| | | |
|---|---|---|
| 0524093 | 1/1993 | European Pat. Off. . |
| 92/09589 | 6/1992 | WIPO . |

OTHER PUBLICATIONS

Zalipsky, et al, Eur. Poly. J., vol. 19, No. 12, pp. 1177–1183 (1983).
Ouchi et al, Drug Design and Discovery, vol. 9, pp. 93–105 (1992).
Mathew et al., J. Med. Chem., 35, 145–151 (1992).
Cecchi et al, J. Med. Chem., 24, 622–625 (1981).
Weiner et al, Journal of Medicinal Chemistry, vol. 16, No. 5, 573–574 (1973).
Nicolaou et al, Nature, vol. 364, 464–466, Jul. (1993).
Commercom et al, Tetrahedron Letters, vol. 33, No. 36, pp. 5185–5188 (1992).
Magri et al, J. Org. Chem., 51, 797–802 (1986).
Gueritte et al, J. Med. Chem., 34, 992–998 (1991).

Primary Examiner—Ba Kim Trinh
Attorney, Agent, or Firm—Steinberg, Raskin & Davidson, P.C.

[57] ABSTRACT

Disclosed are 7-substituted taxoid derivatives, in particular taxol-7-carbazates which have improved water-solubility and/or enhanced therapeutic activity and methods of making the same. The preferred taxoid derivatives have the formula:

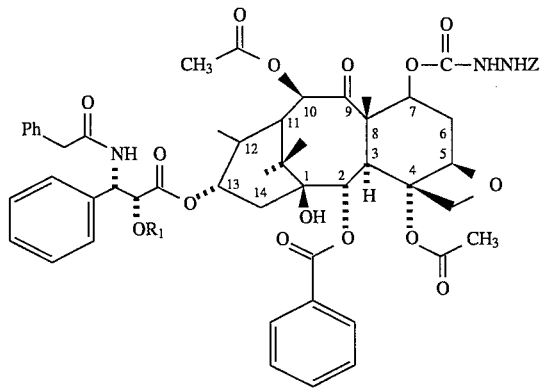

wherein Z is H or

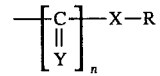

Y=O or S; X=$CH_2$ or O; n=zero or a positive integer, preferably one; with the proviso that when n=0, X=$CH_2$; R=$C_1$–$C_4$ alkyl, haloalkyl, carboxyalkyl, thioalkyl, sulfonylalkyl, phenyl, hydroxyphenyl, aminophenyl, carboxyphenyl, a polyalkyleneoxide homopolymer or water soluble polyalkyleneoxide containing copolymer, having a molecular weight of from about 1,000 to about 20,000;

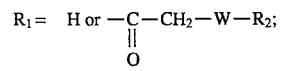

W=O, N—L, S or $SO_2$;

Ph is a phenyl group; L=H, $C_1$–$C_4$ alkyl or phenyl; and $R_2$=$C_{1-C4}$ alkyl, phenyl or a polyalkyleneoxide homopolymer or water soluble polyalkyleneoxide containing copolymer, having a molecular weight of from about 1,000 to about 20,000.

14 Claims, No Drawings

TAXOL-7-CARBAZATES

CROSS REFERENCE TO RELATED APPLICATIONS

This application is a continuation-in-part of U.S. patent application Ser. No. 08/140,346 filed Oct. 20, 1993, now abandoned and a continuation-in-part of U.S. patent application Ser. No. 08/028,743 filed Mar. 9, 1993, now abandoned.

BACKGROUND OF THE INVENTION

The invention pertains to compounds having antimicrotuble activity which are taxoid-based derivatives and demonstrate prolonged anti-neoplastic activity and/or improved water solubility. More particularly, the invention is directed to taxol derivatives which are substituted in the 7-position with a substituted hydrazide or carbazate.

Taxol, or paclitaxel has been investigated as an anticancer agent. It is a plant product derived in minute quantities from the needles and bark of the western pacific yew, *Taxus brevifolia*. The pacific yew is a rare, slow-growing tree which is not typically cultivated. Taxol is a potent inhibitor of cell replication. It is known as an antimicrotuble agent and is believed to inhibit cell mitosis through the enhancement of the rate of microtubular assembly in vitro. This induced aggregation of microtubules is irreversible and microtubular depolymerization is effectively prevented. Numerous studies indicate that the agent has potent cytotoxic activity against a range of human malignancies including breast cancer, metastatic melanomas and ovarian carcinomas. It has also demonstrated antileukemic and tumor inhibitory properties. It is furthermore known that combinations of taxol and radiation therapy have more than an additive interaction effect in inhibiting cell mitosis. Unfortunately the general use of taxol in anticancer therapy has been severely limited by short supply, poor water solubility and immunogenicity. In addition, the anti-neoplastic portions of the western pacific yew tree are very minute and extraction of these portions is complicated and costly. One solution to the problem of short supply has been suggested in U.S. Pat. No. 5,019,504 which discloses an artificial media for producing certain desirable alkaloids. Alternatively, synthetic derivations such as taxotere and taxol intermediates have also been reported, for example, in U.S. Pat. No. 5,015,744.

Hypersensitivity reactions from taxol administration are also known. These include gastrointestinal toxicity and abdominal pain. See J. Clin. Oncol. 8:1263–1268 (1990). Since taxoids are usually extracted from a natural plant source, some hypersensitivity is expected. However, certain non-aqueous vehicles which have been used to overcome the water solubility problems of taxol have also been implicated in causing these hypersensitivity reactions. Therefore, although taxoids hold promise as therapeutic agents, there is a need to provide taxoid-based derivatives which are more water soluble and/or are more active against a wider range of virulent neoplasms than taxol. The present invention provides such a water soluble form of taxol.

SUMMARY OF THE INVENTION

The invention provides a taxoid derivative compound, comprising a taxoid whose 7-position is substituted with a moiety of the formula:

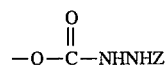

wherein Z is H or

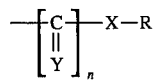

Y=O or S

X=$CH_2$ or O n=zero or a positive integer, preferably one; with the proviso that when n=O, X=$CH_2$; and R=$C_1-C_4$ alkyl, haloalkyl, carboxyalkyl, thioalkyl, sulfonylalkyl, phenyl, hydroxyphenyl, aminophenyl, carboxyphenyl, a polyalkyleneoxide homopolymer or water soluble polyalkyleneoxide containing copolymer, having a molecular weight of from about 1,000 to about 20,000.

More particularly, the invention provides a compound of the formula:

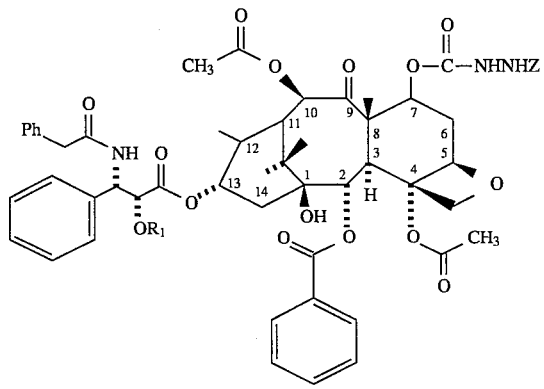

wherein Z is H or

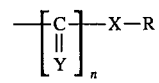

Y=O or S;

X=$CH_2$ or O n=zero or a positive integer, preferably one; with the proviso that when n=O, X=$CH_2$;

R=$C_1-C_4$ alkyl, haloalkyl, carboxyalkyl, thioalkyl, sulfonylalkyl, phenyl, hydroxyphenyl, aminophenyl, carboxyphenyl, a polyalkyleneoxide homopolymer or water soluble polyalkyleneoxide containing copolymer, having a molecular weight of from about 1,000 to about 20,000;

Ph is a phenyl group;

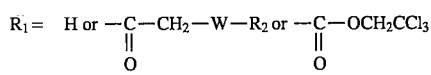

W=O, N—L, S or $SO_2$,

L=H, $C_1-C_4$ alkyl or phenyl, and $R_2$=$C_1-C_4$ alkyl, phenyl or a polyalkyleneoxide homopolymer or water soluble polyalkyleneoxide containing copolymer, having a molecular weight of from about 1,000 to about 20,000.

The invention also provides a method for preparing a taxoid derivative compound, comprising first reacting a taxoid with a reagent under conditions sufficient to modify the 2' hydroxyl with a protecting group moiety of the formula:

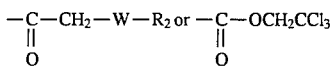

wherein W=O, N—L, S or $SO_2$,

L=H, $C_{1-C4}$ alkyl or phenyl, and $R_2=C_{1-C4}$ alkyl, phenyl or a polyalkyleneoxide homopolymer or water soluble polyalkyleneoxide containing copolymer, having a molecular weight of from about 1,000 to about 20,000;

and then reacting the product with a reagent under conditions sufficient to modify the 7-position with a moiety of the formula:

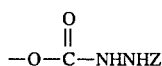

wherein Z is H or

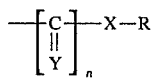

Y=O or S

X=$CH_2$ or O n=zero or a positive integer, preferably one; with the proviso that when n=O, X=$CH_2$; and R=$C_{1-C4}$ alkyl, haloalkyl, carboxyalkyl, thioalkyl, sulfonylalkyl, phenyl, hydroxyphenyl, aminophenyl, carboxyphenyl, a polyalkyleneoxide homopolymer or water soluble polyalkyleneoxide containing copolymer, having a molecular weight of from about 1,000 to about 20,000;

and then optionally reacting the resulting compound with a reagent under conditions sufficient to remove the protecting group moiety and restoring the 2' hydroxyl group.

DETAILED DESCRIPTION OF THE INVENTION

The taxoid-based compositions of the present invention contain carbazate substituents in the 7 position of the taxoid. These substitutions increase water solubility and/or improve therapeutic activity when compared to the corresponding non-7-substituted taxoid compositions. For purposes of the present invention, the term "taxoid" includes all compounds within the taxane family of terpenes. Thus taxol (paclitaxel), 3'-substituted tert-butoxy-carbonyl-amine derivatives (taxoteres) and the like as well as other analogs are within the scope of the invention. Throughout the disclosure, the invention is described with reference to taxol for illustrative purposes. It is to be understood that the modifications described herein are suitable for all taxoids, taxoteres and related molecules. The only limitation is that the selected taxoid must be capable of undergoing the 7-position modification described herein.

The compositions of the present invention are based on the premise that taxol and taxol-like molecules can be modified in the 7-position to provide improved variations of the naturally occurring terpenoids. The compositions are further described as having an anti-microtubule activity in vivo, especially as such action pertains to oncologic or anti-neoplastic activity as such activity is understood by those of ordinary skill in the art. For example, the compositions in some instances will demonstrate the ability to preferentially bind to and stabilize microtubules, thus interrupting cell mitosis. While not being bound by theory, it is believed that other anti-microtubule or oncolytic effects may also be observed in vivo with one or more of the compositions described herein.

For the purposes of the present invention, the taxoid starting material used in the practice of the invention can be selected from a wide variety of materials in addition to taxol per se. Such include, for example, those synthetic taxoids produced commercially by Calbiochem Corp. of San Diego, California and PHYTOpharmaceuticals Corp. of San Carlos, Calif. For ease of description in the present invention, "taxol" will be understood to include all naturally occurring terpenoids as well as all synthetic and related moieties. A non-limiting list of suitable taxol-based compounds are described in Biochem. Biophys. Res. Comm. 124, 329 (1984); J. Med. Chem. 35, 145 (1992); J. of Nat'l Prod. 51, 298 (1988); J. Med. Chem. 32,788 (1989) and S. B. Horowitz, et al Annals NY Acad. of Sci. 466, 733 (1986), all of which are incorporated herein by reference.

The artisan can also synthesize anti-micro tubule compounds such as taxotere as needed. Furthermore, 2'-taxol esters can also be used. Since esters hydrolyze in the acidic environment of cancer cells, 2'-taxol esters are useful as a pro-drug. See J. Med. Chem. 32,788 (1989). While such pro-drug modifications are desirable in certain situations, it has been surprisingly found that the modifications described herein which are realized by conversion of the 7-OH to relatively stable carbazates provides novel compositions which are chemotherapeutically active. Moreover, 2'-taxol esters can be modified in the 7-position if desired, to provide compositions which display both the prodrug and 7-carbazate features.

In addition to the preferred taxol compounds described above, others having anti-microtubule activity in mammals such as vinca alkaloids are modifiable as described herein. A review of antimicrotubule agents is set forth in Pharmac. Ther. 52, pp. 35–84 (1991), the text of which is hereby incorporated by reference.

In the preparation of the inventive compounds, one begins with the taxoid of choice, which is exemplified by taxol having the general formula:

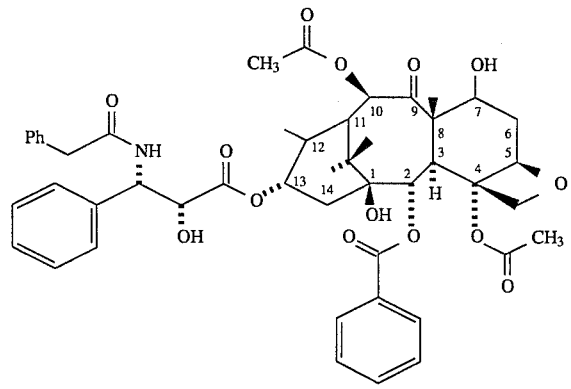

In order to effect 7-position modification, the 2'-position must first be blocked. This is done because the reactivity of the 2'-OH group is much higher than that in the 7-OH of taxol. The taxol is reacted with a reagent to provide a 2'-position protecting group to produce the intermediate:

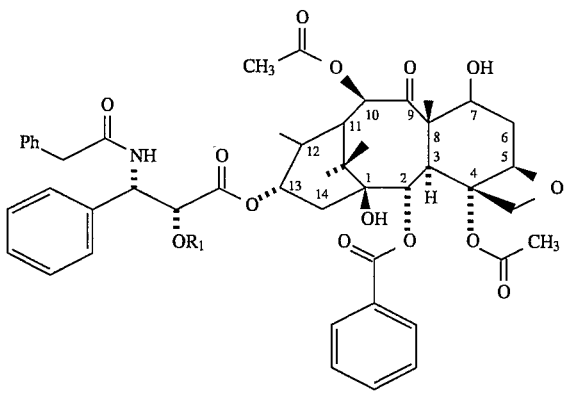

wherein $R_1$ is as defined above. Such 2'-substituted taxoid derivatives can be prepared by reacting the taxol with an ester or carbonate forming reagent having the structure:

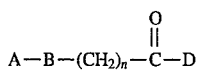

wherein
n=zero or a positive integer;
B=oxygen, NL where L is selected from the group consisting hydrogen, $C_{1-4}$ alkyls, S or $SO_2$;
A=$C_{1-12}$ alkyl, substituted alkyls, phenyl or a polyalkyleneoxide. The alkyl substitution can include one or more hydroxy, amino, alkylthio, aryl or aralkyl moieties. When n=O and B is oxygen, carbonates are formed in the 2'-position of the taxoid. Other simple 2'-position carbonates containing alkyl or aralkyl moieties are possible using $C_{1-12}$ and preferably trichloroethoxy, $C_{1-4}$ alkyl or substituted alkyl groups. Among the polyalkylene oxides (PAO's), mono-activated, alkyl-terminated PAO's such as monomethyl-terminated polyethylene glycols (mPEG's) are preferred. Bis-activated polyethylene oxides are also contemplated for purposes of cross-linking taxoids or providing a means for attaching other moieties such as targeting agents. Although polyethylene glycols vary substantially by weight, polymers having molecular weight ranges of from about 200 to about 20,000 are usually selected for the purposes of the present invention. Molecular weights of from about 1,000 to about 12,000 are preferred and 2,000 to about 5,000 are particularly preferred. The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained. In addition to mPEG, $C_{1-4}$ alkyl-terminated polymers are also useful.

D is a group capable of being displaced by a nucleophilic reagent. D is preferably selected from halides, N-hydroxysuccinimidyl, N-hydroxybenzotriazolyl, p-nitrophenoxy, imidazolyls and the like. Activated carbonates or acid chlorides are preferred carbonate forming reagents. For the case when n is a positive integer, D can be OH.

The 2'-substitution reaction with the ester or carbonate forming reagent is conducted in the presence of an inert organic solvent such as methylene chloride, toluene, tetrahydrofuran or DMSO and optionally in the presence of a base. The preferred bases are tertiary amines such as triethylamine, diisopropylethylamine and pyridine. Pyridine may also serve as a solvent. The reaction temperature should be below the decomposition temperature of taxol, preferably from about 4° C. to about 115° C., most preferable about 25° to 60° C. The reaction is preferably being conducted with a slight excess of the ester or carbonate forming reagent.

In the preferred embodiment, the protecting group is an activated ester. The formation of an acetate with the 2'-OH may be carried out in the manner described in Biochem. Res. Comm. 124, 329 (1984) or J. Med. Chem. 35, 145 (1992). The most preferred blocking group is methoxyacetate ester. Although the 2'-position is much more reactive than the 7-position, with some reagents a small amount of 2', 7-position disubstitution is also noticed at this stage. It has been found that the N-hydroxysuccinimidyl ester of methoxy acetic acid reacts exclusively at the 2'-position. When A=polyalkylene oxide and n=a positive integer, the preferred method of synthesis of the ester is to condense the polyalkylene oxide acid directly with taxol employing reagents such as dicyclohexylcarbodiimide in an inert solvent.

Once the 2'-position of the taxoid has been protected or substituted, the 7-position can be functionalized by reacting a 2'-protected taxoid with a formate derivative which reacts with alcohols to form an intermediate, and then with hydrazine or a hydrazine derivative to form the carbazate.

In the preferred embodiment, the 2'-substituted-taxol is reacted with carbonyldiimidizole, bis-succinimidyl carbonate, or phosgene or derivative thereof such as triphosgene and paranitrophenylchloroformate to produce the formate intermediate. The formate intermediate is then reacted with hydrazine or a hydrazine derivative to produce the 2'-substituted-7-substituted carbazate. The preferred reagents for this step are hydrazine, alkylhydrazine, acetic hydrazide, t-butyl carbazate, polyethylene glycol hydrazide or polyethylene glycol carbazate having molecular weights of from about 1,000 to about 20,000, and t-butyl-hydrazate. The polyalkyleneoxide moieties include all of those listed above as substituents at the 2'-position.

The reaction is conducted in one of the above mentioned inert solvents, under a nitrogen blanket to maintain anhydrous conditions. The reaction proceeds for from about 8 to about 24 hours at a temperature under the decomposition temperature of the intermediate, and preferably in the range of from about 65° C. to about 130° C. The reaction can be promoted by use of a base catalyst. After the 7-position modification, the 2'-protective group can be removed with an equivalent of a nucleophile such as a primary amine, e.g ethanolamine to return the OH group to the 2'-position. Should it be desired to remove the protective group by an acid treatment, the preferred blocking reagent is 2,2,2-trichloroethylcarbonate.

Another aspect of the present invention provides methods of treatment for various medical conditions in mammals. The methods include administering an effective amount of a modified taxoid which has been prepared as described herein to the mammal. The compositions are useful for, among other things, treating neoplastic disease, reducing tumor burden, preventing metastasis of neoplasms and preventing recurrences of tumor/neoplastic growths.

The amount of modified taxoid used in the treatment methods is generally described as that amount which effectively achieves the desired therapeutic result in mammals. Naturally, the dosages of the various modified taxoids will vary somewhat depending upon the taxoid moiety and the modifications made at the 7 position. In general, however, modified taxoid is administered in amounts ranging from about 5 to about 500 mg/m² per day, based on the amount of the taxoid moiety in the conjugate. The range set forth above is illustrative and those skilled in the art will determine the optimal dosing of the conjugate selected based on clinical experience and the treatment indication.

The modified taxoid of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan.

The following non-limiting examples serve to illustrate the invention.

EXAMPLE 1

Preparation of Taxol 2'-methoxyacetate
(2'-MAc-taxol)

A. The N-Hydroxysuccinimidyl ester of methoxyacetic acid (MAc-NHS) is prepared as follows. N-Hydroxysuccinimide (2.53 g, 22.0 mmol) is suspended in 10 mL of methylene chloride along with methoxyacetyl chloride (2.17 g, 20.0 mmol). Thereafter, a solution containing diisopropylethylamine (2.84 g, 22.0 mmol) in 15 mL of methylene chloride is added. After stirring at room temperature for 4 hours, the reaction mixture is washed with water, dried over sodium sulfate and evaporated to dryness. The crude product is recrystallized from 1:1 ethyl acetate-hexane (yield 2.4 g, 64%). The product is characterized by IR, NMR and elemental analysis.

B. Taxol 2'-methoxyacetate (2'-MAc-taxol) is prepared by heating taxol (100 mg, 0,117 mmol) with MAc-NHS (86 mg, 0.46 mmol) in 1 mL anhydrous pyridine at 60° C. until more than 99% of the taxol is converted to the product. 11 mg of methanol is added to the reaction mixture and after 15 minutes, dissolved in methylene chloride and subjected to the work up procedure as described above (yield 95 mg, 88%). The product is characterized by NMR and FAB-mass spectra.

EXAMPLE 2

Taxol-7-OCONHNHCOOPEG2000

2'-MActaxol (50mg, 0.049mmol) is dissolved in anhydrous methylene chloride (4 ml) under a nitrogen atmosphere. To this solution is added anhydrous pyridine (160 microliters) followed by the addition of triphosgene (50 mgs). The reaction is monitored by HPLC (C8 column, methanol:water, 80:20 v:v as eluent) until the formation of the chloroformate is complete. To the reaction mixture is added PEG2000—O—CO—NHNH₂ (PEG-carbazate) (200mg) in methylene chloride (3 ml) and the reaction mixture is stirred at room temperature for 2 hours. The reaction mixture is worked up by washing the mixture with water (5 ml). The organic layer is dried with anhydrous sodium sulfate and evaporated under vacuum to give a solid which is purified by HPLC reverse phase column using methanol:water (70:30) v:v as mobile phase. This product is treated with ethanolamine (100 microliters) in 3 ml of 2-propanol for 2 hours to remove the MAc group. The reaction is worked up by washing the reaction mixture with water (5 ml). The organic layer is dried with anhydrous sodium sulfate and evaporated to give the taxol-7-OCONHNHCOOPEG as a white solid.

EXAMPLE 3

Taxol-7-OCONHNHCOOPEG5000

2'-MActaxol (50 mg, 0.049mmol) is dissolved in anhydrous methylene chloride (4 ml) under a nitrogen atmosphere. To this solution is added anhydrous pyridine 160 microliters) followed by the addition of triphosgene (50 mgs). The reaction is monitored by HPLC (C8 column, methanol:water, 80:20v:v as eluent) until the formation of the chloroformate is complete. To the reaction mixture is added PEG5000-O-CO-NHNH₂ (PEG-carbazate) (200 mg) in methylene chloride (3 ml) and the reaction mixture is stirred at room temperature for 2 hours. The reaction mixture is worked up by washing the mixture with water (5 ml). The organic layer is dried with anhydrous sodium sulfate and evaporated under vacuum to give a solid which is purified by HPLC reverse phase column using methanol:water (70:30) v:v as mobile phase. This product is treated with ethanolamine (100 microliters) in 3 ml of 2-propanol for 2 hours to remove the MAc group. The reaction is worked up by washing the reaction mixture with water (5 ml). The organic layer is dried with anhydrous sodium sulfate and evaporated to give the taxol-7-OCONHNHCOOPEG as a white solid. The solubility of the 5 kD PEG derivative is estimated by adding water in small portions to 100 mg of substance, until dissolution occurs. About 100 microliters of water gives a clear, but extremely viscous solution. An additional 50 microliters of water gives a flowable liquid and this total volume is used for calculations. Based on the value of 150 microliters, the solubility of the PEG compounds is calculated to be minimally 666 mg/mL. In contrast, the solubility of taxol is <.01 mg/ml.

EXAMPLE 4

Taxol-7-OCONHNHCOCH₃

2'-MActaxol (30 mg) is dissolved in anhydrous methylene chloride (4 ml) and to this solution is added anhydrous pyridine (80 microliters) under nitrogen atmosphere, followed by the addition of triphosgene (30 mg). The reaction is monitored by HPLC using a reverse phase C8 column and methanol:water 80:20 (v:v) as eluent until the formation of the chloroformate is complete. To the reaction mixture is added acetohydrazide (5 mg) in 1 ml of methylene chloride. The reaction mixture is stirred at room temperature for 2 hours. The reaction is worked out as described in Example 1 followed by the deprotection with ethanolamine to give the product. ¹HNMR (CDCl₃)δ:8.1 (m.3'nBZ), 7.92 (m, 2'OBZ), 7.3–7.7(m) all other aromatic H,7 (m,3'NH), 6.2 (m), 5.8 (d), 5.6 (d of d), 5.4 (m), 4.9 (d), 4.8 (s), 4.1–4.4 (ABq), 1.1–2.5 (8 peaks) ppm.

EXAMPLE 5

Preparation of
2'-Methoxyacetyl-7-carbonylimidazolyl Taxol
(2'-MAc-7-CI)

In a 25 mL round bottomed flask is placed 2'-MAc-taxol (102 mg, 0.11 mmol), carbonyldiimidazole (53 mg, 0.33 mmol) and methylene chloride (5 mL). The resulting clear solution is stirred at room temperature under a nitrogen atmosphere for 5 hours when HPLC shows complete disappearance of 2'-MAc-taxol. The reaction mixture is diluted with 50 mL of methylene chloride, washed with 2×50 mL of water, dried over magnesium sulfate, and evaporated to dryness. The crude product thus obtained (105 mg, 94%) is used without further purification for the preparation of 7-substituted taxol deriatives. The FAB-MS gives m+1 peak at 1020.3, whereas the theoretical value is 1020.36.

EXAMPLE 6

Taxol-7-OCONHNH$_2$

2'-MAc-7-CI taxol (24 mg, 0.023 mmol) is dissolved in 1 ml of anhydrous 2-propanol and to this solution is added hydrazine (2 mg) under nitrogen atmosphere. The reaction is monitored by HPLC using a C8 reverse phase column and methanol:water (80:20) (v:v) as eluent. The reaction mixture is stirred for 18 hours at 50° C. and the solvent is removed under vacuum. The residue obtained is diluted with methylene chloride and washed with water (5 ml). The organic layer is dried with anhydrous sodium sulfate and solvent is evaporated to give a solid which is purified by HPLC using a reverse phase C8 column and methanol:water 80:20 (v:v) as mobile phase.

What is claimed is:

1. A taxane derivative compound of the formula:

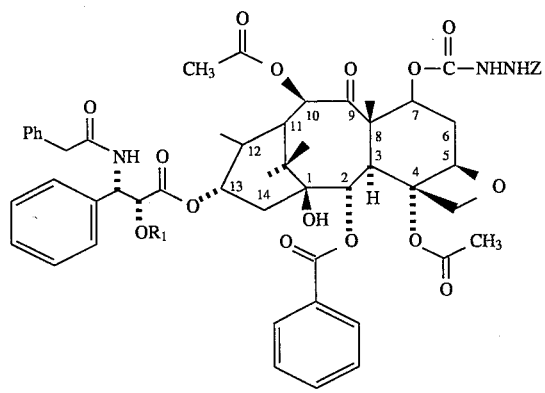

wherein Z is

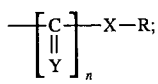

Y=O or S;

X=CH$_2$ or O;

n=a positive integer;

R=C$_1$–C$_4$ alkyl, haloalkyl, carboxyalkyl, thioalkyl, sulfonylalkyl, phenyl, hydroxyphenyl, aminophenyl, carboxyphenyl, a polyalkyleneoxide homopolymer or water soluble polyalkyleneoxide containing copolymer, having a molecular weight of from about 1,000 to about 20,000;

Ph is a phenyl group:

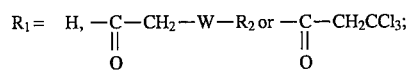

W=O, N—L, S or SO$_2$,

L=H, C$_1$–C$_4$ alkyl, phenyl;

R$_2$=C$_1$–C$_4$ alkyl, phenyl or a polyalkyleneoxide homopolymer or water soluble polyalkyleneoxide containing copolymer, having a molecular weight of from about 1,000 to about 20,000.

2. The taxane derivative compound of claim 1, wherein Y=oxygen.

3. The taxane derivative compound of claim 1, wherein n=1.

4. The taxane derivative compound of claim 1, wherein R is a polyalkyleneoxide.

5. The taxoid derivative compound of claim 4, wherein R is a polyalkyleneoxide having a terminal alkyl group.

6. The taxoid derivative compound of claim 5, wherein R is a monomethyl-terminated polyethylene glycol.

7. The taxane derivative compound of claim 1, wherein R is a polyalkyleneoxide homopolymer having a molecular weight of from about 2,000 to about 5,000.

8. A method of treating neoplastic disease, tumor burden, metastasis of neoplasms and recurrences of tumor or neoplastic growths in a mammal, comprising administering a pharmaceutically effective dose of the taxane derivative compound of claim 1 to such mammal.

9. A taxane compound of the formula:

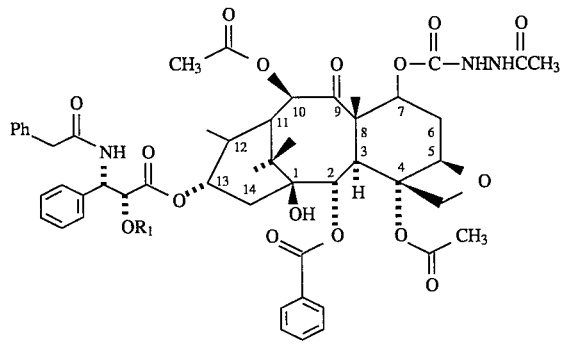

wherein

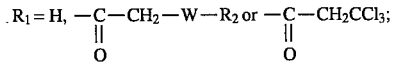

W=O, N—L, S or SO$_2$;

L=H, C$_1$–C$_4$ alkyl or phenyl;

R$_2$=C$_1$–C$_4$ alkyl, phenyl or a water soluble polyalkyleneoxide having a molecular weight of from about 1,000 to about 20,000.

10. A method of preparing a taxane 7-carbazate, comprising:

a) dissolving a composition of the formula:

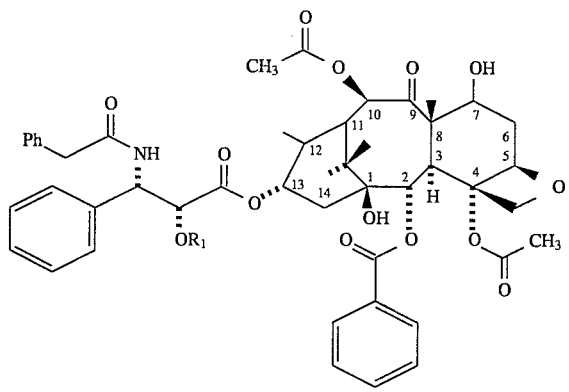

wherein:

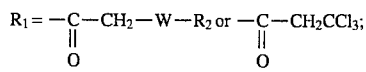

W=O, N—L, S or SO$_2$;

L=H, C$_1$–C$_4$ alkyl or phenyl;

R$_2$=C$_1$–C$_4$ alkyl, phenyl or a water soluble polyalkyleneoxide having a molecular weight of flora about 1,000 to about 20,000 in an inert solvent;

b) reacting said dissolved composition of step a) with a member of the group consisting of carbonyldiimidazole, bis-succinimidyl carbonate, phosgene, phosgene derivatives, and paranitrophenylchloroformate and c) reacting the product of step b) with a hydrazine derivative selected from the group consisting of acetic hydrazide, t-butyl carbazate, polyethylene glycol hydrazide and polyethylene glycol carbazate.

11. The compound of claim 1, wherein said taxane derivative compound is taxol-7-carbazate.

12. The method of claim 8, wherein said taxane derivative compound is taxol-7-carbazate.

13. The method of claim 8, wherein said taxane derivative compound is administered in an amount of from about 5 to about 500 mg/m$^2$ per day.

14. A taxane compound of the formula:

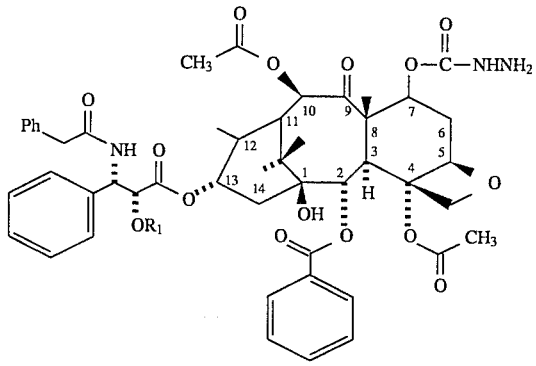

wherein

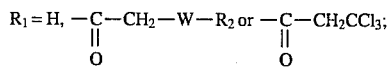

W=O, N–L, S or SO$_2$;

L=H, C$_1$–C$_4$ alkyl or phenyl;

R$_2$=C$_1$–C$_4$ alkyl, phenyl or a water soluble polyalkyleneoxide having a molecular weight of from about 1,000 to about 20,000.

* * * * *

UNITED STATES PATENT AND TRADEMARK OFFICE
CERTIFICATE OF CORRECTION

Page 1 of 6

PATENT NO. : 5,547,981
DATED : Aug. 20, 1996
INVENTOR(S) : Richard B. Greenwald, Annapurna Pendri It is certified that error appears in the above-identified patent and that said Letters Patent are hereby corrected as shown below:

Column 2, line 23; Column 9, line 28; and the Abstract

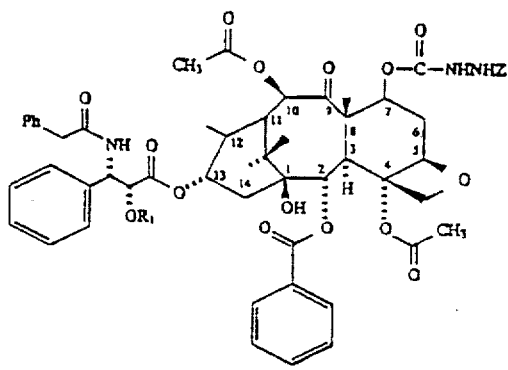

should read

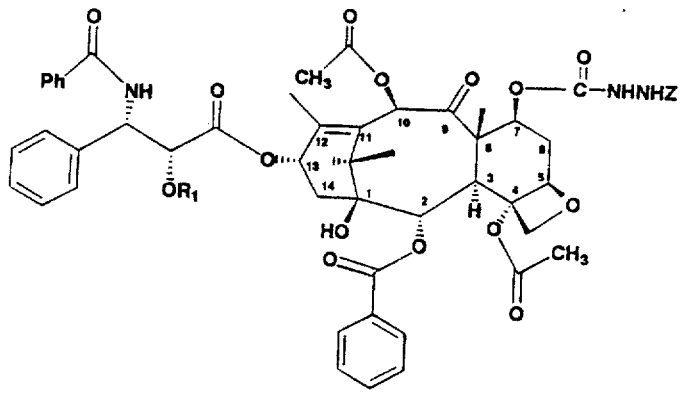

UNITED STATES PATENT AND TRADEMARK OFFICE
CERTIFICATE OF CORRECTION

PATENT NO. : 5,547,981

DATED : Aug. 20, 1996

INVENTOR(S) : Richard B. Greenwald, Annapurna Pendri

It is certified that error appears in the above-identified patent and that said Letters Patent are hereby corrected as shown below:

Column 4, line 49

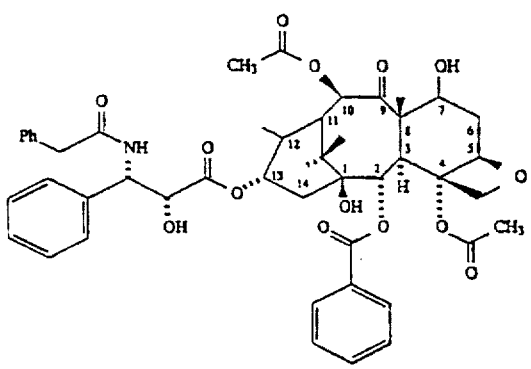

should read

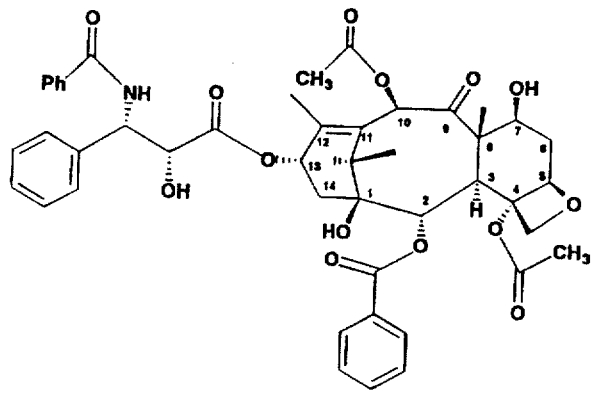

UNITED STATES PATENT AND TRADEMARK OFFICE
CERTIFICATE OF CORRECTION

PATENT NO.  : 5,547,981
DATED       : Aug. 20, 1996
INVENTOR(S) : Richard B. Greenwald, Annapurna Pendri It is certified that error appears in the above-identified patent and that said Letters Patent are hereby corrected as shown below:

Column 5 line 3; and Column 11, line 2

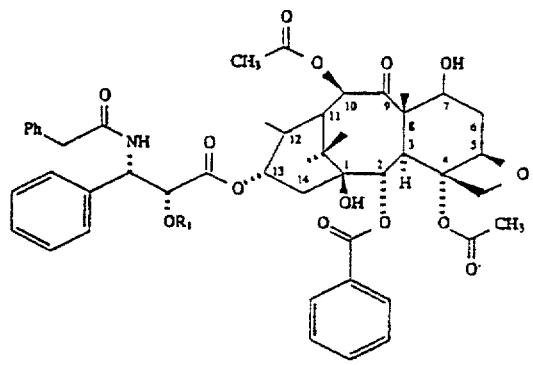

should read

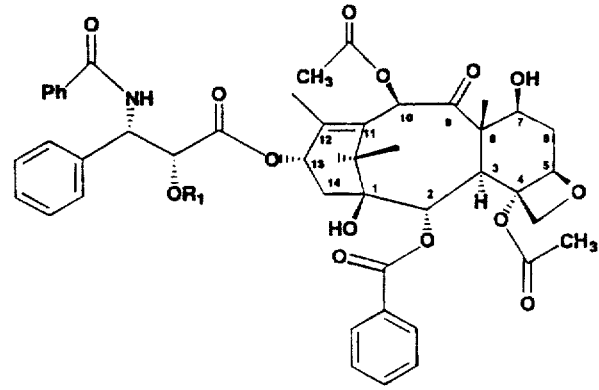

UNITED STATES PATENT AND TRADEMARK OFFICE
CERTIFICATE OF CORRECTION

PATENT NO. : 5,547,981
DATED : Aug. 20, 1996
INVENTOR(S) : Richard B. Greenwald, Annapurna Pendri It is certified that error appears in the above-identified patent and that said Letters Patent are hereby corrected as shown below:

Column 10, line 33

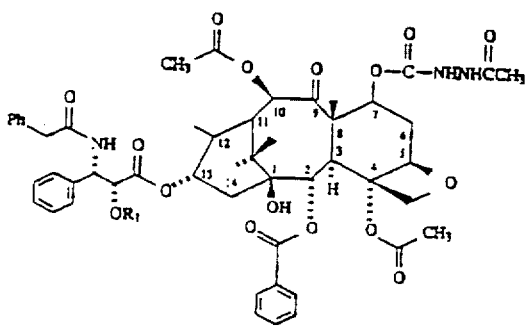

should read

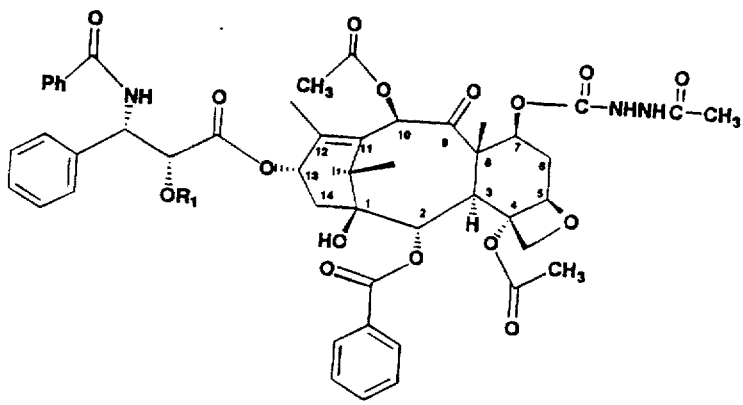

Column 11, line 27 "flora" should read --from--.

UNITED STATES PATENT AND TRADEMARK OFFICE
CERTIFICATE OF CORRECTION

PATENT NO. : 5,547,981

DATED : Aug. 20, 1996

INVENTOR(S) : Richard B. Greenwald, Annapurna Pendri

Page 5 of 6

It is certified that error appears in the above-identified patent and that said Letters Patent are hereby corrected as shown below:

Column 12, line 9

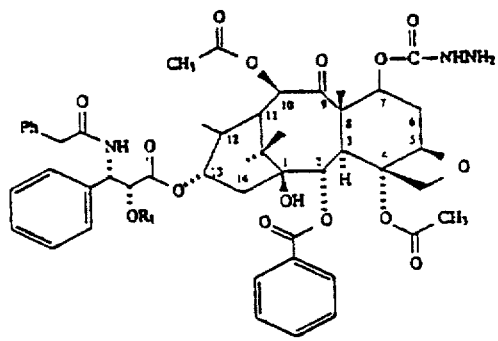

should read

UNITED STATES PATENT AND TRADEMARK OFFICE
CERTIFICATE OF CORRECTION

PATENT NO. : 5,547,981
DATED : Aug. 20, 1996
INVENTOR(S) : Richard B. Greenwald, Annapurna Pendri It is certified that error appears in the above-indentified patent and that said Letters Patent is hereby corrected as shown below:

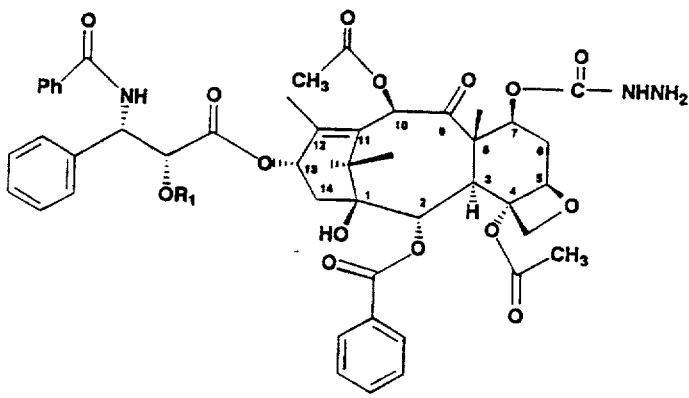

Signed and Sealed this

Fifteenth Day of July, 1997

Attest:

BRUCE LEHMAN

Attesting Officer    Commissioner of Patents and Trademarks